United States Patent
van den Honert

(10) Patent No.: US 9,844,672 B2
(45) Date of Patent: *Dec. 19, 2017

(54) FOCUSED STIMULATION IN A MEDICAL STIMULATION DEVICE

(71) Applicant: Cochlear Limited, Macquarie University, NSW (AU)

(72) Inventor: Christopher van den Honert, Englewood, CO (US)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,220

(22) Filed: Jan. 30, 2017

(65) Prior Publication Data
US 2017/0165487 A1    Jun. 15, 2017

Related U.S. Application Data

(60) Continuation of application No. 12/979,676, filed on Dec. 28, 2010, now Pat. No. 9,566,433, which is a
(Continued)

(51) Int. Cl.
*A61N 1/00* (2006.01)
*A61N 1/36* (2006.01)
(Continued)

(52) U.S. Cl.
CPC ....... *A61N 1/36032* (2013.01); *A61N 1/0541* (2013.01); *A61N 1/323* (2013.01);
(Continued)

(58) Field of Classification Search
CPC .. A61N 1/36032; A61N 1/0541; A61N 1/323; H04R 25/305; H04R 25/606
See application file for complete search history.

(56) References Cited

U.S. PATENT DOCUMENTS

| 4,532,930 A | 8/1985 | Crosby et al. |
| 4,648,403 A | 3/1987 | Van Compernolle |

(Continued)

FOREIGN PATENT DOCUMENTS

| WO | 0113991 A1 | 3/2001 |
| WO | 061190069 A2 | 11/2006 |

OTHER PUBLICATIONS

International Searching Authority, International Search Report, issued in connection with International Patent No. PCT/US2010/023191, dated Mar. 31, 2010 (4 pages).
(Continued)

*Primary Examiner* — Mallika D Fairchild
(74) *Attorney, Agent, or Firm* — Edell, Shapiro & Finnan, LLC

(57) ABSTRACT

A medical stimulation device such as a cochlear implant configured to provide stimulation of one or more spatially-restricted contiguous portion(s) of the spiral array of auditory nerve fibers in the cochlear ("discrete stimulation regions"). Each discrete stimulation region is defined by the constructive and/or destructive interference of stimulating and limiting signals simultaneously applied to electrode channels of an implanted electrode array, the stimulating and limiting signals being determined based upon transimpedance measurements of intracochlear electrode channels of the implanted electrode array representing specific spread functions of an individual recipient.

21 Claims, 6 Drawing Sheets

Related U.S. Application Data division of application No. 11/414,360, filed on May 1, 2006, now Pat. No. 7,860,573.

(60) Provisional application No. 60/675,860, filed on Apr. 29, 2005.

(51) Int. Cl.
    *A61N 1/05*     (2006.01)
    *A61N 1/32*     (2006.01)
    *H04R 25/00*     (2006.01)

(52) U.S. Cl.
    CPC ....... *A61N 1/36036* (2017.08); *H04R 25/305* (2013.01); *H04R 25/606* (2013.01)

(56) References Cited

U.S. PATENT DOCUMENTS

| | | |
|---|---|---|
| 6,249,704 B1 | 6/2001 | Maltan et al. |
| 6,537,200 B2 | 3/2003 | Leysieffer et al. |
| 6,565,503 B2 | 5/2003 | Leysieffer et al. |
| 6,575,894 B2 | 6/2003 | Leysieffer et al. |
| 6,594,525 B1 | 7/2003 | Zierhofer |
| 6,594,526 B2 | 7/2003 | Betzold |
| 6,697,674 B2 | 2/2004 | Leysieffer |
| 7,110,821 B1 | 9/2006 | Ross |
| 7,426,414 B1 | 9/2008 | Litvak et al. |
| 2003/0105504 A1 | 6/2003 | Zierhofer |
| 2005/0187592 A1 | 8/2005 | Seligman et al. |
| 2005/0192648 A1 | 9/2005 | Killian et al. |
| 2007/0135862 A1 | 6/2007 | Nicolai et al. |

OTHER PUBLICATIONS

International Searching Authority, "Written Opinion," issued in connection with International Patent Application No. PCT/US2010/023191, dated Mar. 31, 2010 (4 pages).

English language translation of "First Office Action," issued by Chinese Intellectual Property Office, in connection with Chinese Patent Application No. 200680023866.8, dated Jan. 8, 2010 (2 pages).

Norgia et al., "Measurement of Electrode Current Pulses from Cochlear Implants". Proceedings of the 21st IEEE. Como, Italy: IEEE May 18-20, 2004, vol. 3, p. 1697-1700.

Rodenhiser et al. "A Solution to the Inverse Problem: A Method for Determining the Driving Currents for Focused Stimulation". Oct. 31, 1991. New Frontiers of Biomedical Engineering Innovations From Nuclear to Space Technology 13th Annual International Conference of the IEEE Engineering in Medicine and Biology Society: Oct. 31-Nov. 3, 1991, Orlando, Florida, ISA: Proceeding, XP010102083.

Eddington et al. "Auditory Prostheses Research With Multiple Channel Intracochlear Stimulation in Man" . Ann Otol Rhinol Laryngol.; Nov.-Dec. 1978;87(6 Pt 2):5-39.

Shannon, Robert V. "Multichannel electrical stimulation of the auditory nerve in man. I. Basic psychophysics." Hearing Research Aug. 1983;11(2):157-89.

White et al. "Multichannel Cochlear Implants" Archives of Otolaryngol. 1984;110(8):493-501.

Favre et al. "Channel interactions in patients using the Ineraid multichannel cochlear implant." Hearing Research. Apr. 1993;66(2):150-6.

Boex et al. "Electrical field interactions in different cochlear implant systems" J. Acoust. Soc. Am. vol. 114, Issue 4, pp. 2049-2057 (Oct. 2003).

Suesserman et al. "Lumped-parameter model for in vivo cochlear stimulation" IEEE Transactions on Biomedical Engineering. vol. 40, Issue: 3. Publication Date: Mar. 1993. pp. 237-245.

van den Honert et al. "Focused intracochlear electric stimulation with phased array channels" Journal of Acoustic Society America 121(6) Jun. 2007, pp. 3703-3716.

Vanpoucke et al. Identification of the impedance model of an implanted cochlear prosthesis from intracochlear potential measurements IEEE Transactions on Biomedical Engineering. Publication Date: Dec. 2004 vol. 51, Issue: 12. pp. 2174-2183.

International Search Report for PCT/US2006/016353 dated May 17, 2007.

European Search Report for 06751841.5-2305/PCT/US2006016353 dated Nov. 9, 2009.

Van Compernolle, Dirk, Speech Processing Strategies for a Multi-channel Cochlear Prosthesis, Ph.D. Dissertation. Stanford University (1985).

Van Compernolle, Dint, "A computational model of the cochlea used with cochlear prosthesis patients," in: Acoustics, Speech, and Signal Processing, IEEE International Conference on ICASSP '85, vol. 10, pp. 427-429 (1985).

Townshend, et al., "Pitch perception by cochlear implant subjects," J. Acoust. Soc. Am., 82(1): 106-115 (1987).

Townshend B, et al., "Reduction of Electrical Interaction in Auditory Prostheses" IEE Tran. Biomd. Eng. BME-34, No. 11, p. 891-897 (1987).

Rodenhiser, et al., A method for determining the driving currents for focused stimulation in the cochlea, IEEE Tans. Biomd. Eng. 42(4) (Apr. 1995) p. 337-342.

Clopton, et al., "Electrode Configuration and Spread of Neural Excitation: Compartmental Models of Spiral Ganglion Cells," Clark & Cowan, International Cochlear Implant, Speech and Hearing Symposium. 1995 Ann Otol Rhino'. Laryngol. Suppl. 166, 115-118.

Jolly, et al., "Quadrupolar Stimulation for Cochlear Prostheses: Modeling and Experimental Data," IEEE Trans. Blomd. Eng., vol. 43, No. 8, (Aug. 1996), p. 857-885.

Kral, et al., Spatial resolution of cochlear Implants: the electrical field and excitation of auditory afferents, Hearing Research 121 (1998), 11-28.

Miyoshi, et al., "Proposal of a New Auditory Nerve Stimulation Method for Cochlear Prosthesis," Artificial Organs, 20 (8): 941-946, 1996.

White, et al., "Current Spreading and Speech-Processing Strategies for Cochlear Prostheses," Clark & Busby, International Cochlear Implant Symposium, pp. 22.24, Ann Otol. Rhino Laryng. 96 (Suppl. 128), 1987.

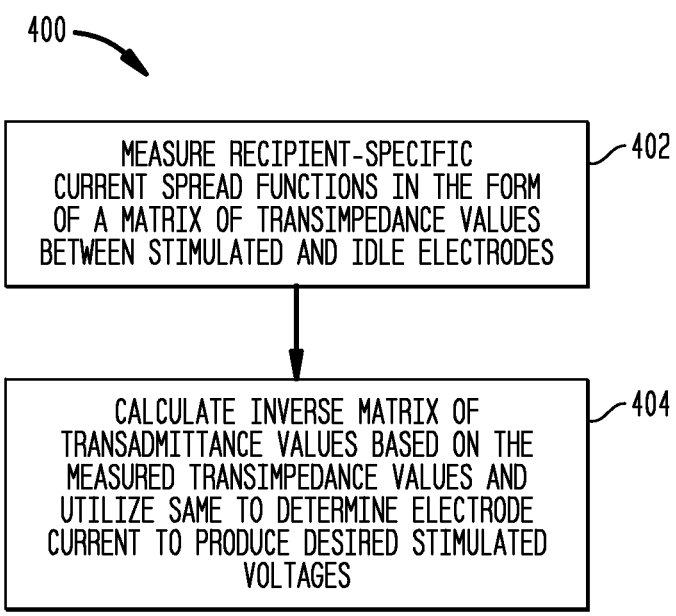

$$512_1 \{ V_1 = Z_{1,1}I_1 + Z_{2,1}I_2 + Z_{3,1}I_3 \ldots + Z_{22,1}I_{22}$$
$$512_2 \{ V_2 = Z_{1,2}I_1 + Z_{2,2}I_2 + Z_{3,2}I_3 \ldots + Z_{22,2}I_{22}$$
$$\vdots \quad \vdots \quad \vdots \quad \vdots \quad \ddots \quad \vdots$$
$$512_{22} \{ V_{22} = Z_{1,22}I_1 + Z_{2,22}I_2 + Z_{3,22}I_3 \ldots + Z_{22,22}I_{22}$$

FOCUSED STIMULATION IN A MEDICAL STIMULATION DEVICE

CROSS-REFERENCE TO RELATED APPLICATIONS

This application is a continuation application of U.S. patent application Ser. No. 12/979,676, entitled "Focused Stimulation in a Medical Stimulation Device," filed on Dec. 28, 2010, which is a divisional of U.S. patent application Ser. No. 11/414,360, entitled "Focused Stimulation in a Medical Stimulation Device", filed on May 1, 2006, now issued as U.S. Pat. No. 7,860,573, which claims priority from U.S. Provisional Patent Application No. 60/675,860 entitled, "Phased Array Stimulation," filed Apr. 29, 2005, all of which are hereby incorporated by reference herein.

BACKGROUND

Field of the Invention

The present invention relates generally to medical stimulation devices, and more particularly, to focused stimulation in a medical stimulation device.

Related Art

There are several types of medical devices that use electrical signals to activate nerve, muscle or other tissue fibers in a recipient (also referred to herein as a user, listener, patient, etc.; "recipient" herein) to stimulate an activity. Such medical devices are generally referred to herein as medical stimulation devices. Usually the activity is invoked to compensate for a deficiency in the recipient. For example, stimulating prosthetic hearing devices have been developed to compensate for loss of hearing.

Several types of prosthetic hearing devices provide electrical stimulation to aid recipients who have a hearing deficiency. For example, Cochlear™ implants (also referred to as Cochlear™ devices, Cochlear™ prosthetic devices, Cochlear™ implants, and the like; simply "cochlear implants" herein) apply one or more stimulating signals to the cochlea of a recipient to stimulate hearing. Another example is an auditory brain implant that delivers electrical stimulation to the auditory brainstem nuclei of a recipient to stimulate hearing. For ease of description, the present invention is presented in the context of a prosthetic hearing device, namely, a cochlear implant. However, it should be appreciated that unless stated otherwise, the present invention is applicable to any medical stimulation device now or later developed.

Cochlear implants typically include a sound transducer that receives incoming sound, and a sound processor that converts selected portions of the incoming sound into corresponding stimulating signals based on an implemented sound encoding strategy. The sound processor transmits the stimulating signals along an electrode array implanted within or adjacent to the cochlea of the recipient.

Cochlear implants exploit the tonotopic organization of the cochlea by mapping audio energy in specific frequency bands to deliver stimulation at corresponding locations along the spiral array of auditory nerve fibers. To achieve this, the processing channels of the sound processor; that is, specific frequency bands with their associated signal processing paths, are mapped to a set of one or more electrodes to stimulate a desired nerve fiber or nerve region of the cochlear. Such sets of one or more electrodes are referred to herein as "electrode channels" or, more simply, "channels."

Conventional cochlear implants have limitations that may produce undesirable effects for recipients. One fundamental problem that limits the spatial resolution of multi-channel cochlear implants is referred to as "current spread" and is illustrated in FIG. 1. Although stimulation through one channel is intended to excite a single nerve region, in fact the actual locus of neural excitation can be broad and complex due the spread of current throughout the conducting fluids and tissues of the cochlea.

FIG. 1 is a graph illustrating the voltage created at various electrodes in response to the application of current at one electrode. Voltage profile 101 illustrates the voltage created at different nerve regions of the cochlear ("tissue voltage") at a plurality of locations adjacent electrodes 104 of an electrode array 106 in response to current delivered to electrode number 11. Superimposed on FIG. 1 is a illustration of the current spread 102 emanating from the nerve region adjacent electrode 11 which causes voltage profile 101.

As illustrated by voltage profile 101, current delivered by electrode 11 may spread over a potentially wide spatial extent of neighboring nerve regions. This current spread may extend, for example, to nerve regions adjacent to distant electrodes 1 and 22 of the 22 electrodes of electrode array 106. As a result, a stimulating voltage 101 arises not only in the nerve region adjacent electrode 11 but also at more distant nerve regions in the tissue. As shown in FIG. 1, the stimulating voltage 101 is strongest or most intense near electrode 11, dropping off slowly and, in this example, remaining non-negligible at all regions in the cochlea nerve adjacent to electrode array 106. As a result, in addition to the nerve fibers adjacent electrode 11, other nerve fibers in the cochlea are stimulated by current applied to electrode 11. This may produce a distributed place-pitch perception, rather than the single pitch percept that was intended by the stimulating method.

This problem is exacerbated when current flows concurrently from two or more electrodes, as would occur when representing a sound with multiple frequency components. When two or more channels are activated concurrently, the locus of excitation is not the simple union of their individual loci because of the nonlinearity of the neural excitation process. Instead, neurons that fall outside of the individual loci (i.e. those which would not respond to any one channel) may nevertheless be excited by the summed current fields. This results in the well-known phenomenon of "channel interaction" or "channel overlap." Channel interaction can lead to unpredictable loudness fluctuations, and smearing of the spatial representation of spectrum.

FIG. 2 shows the consequences of current spread $202_9$ and $202_{13}$ when current concurrently flows from two electrodes 9 and 13 of electrode array 106. Voltage profile 208 is generated in response to stimulating electrode 9, while voltage profile 210 is generated in response to stimulating electrode 13. Voltage profile 212 is the sum of voltage profiles 208 and 210; that is, voltage profile 212 is generated in response to simultaneously stimulating electrodes 9 and 13. As shown in FIG. 2, the combined currents produce a stimulus voltage in the nerve region adjacent to each electrode which is greater than intended, as well as a high voltage 214 in the nerve region between the electrodes 9 and 13.

This summation of stimulus voltages has many undesirable perceptual consequences, particularly when many electrodes are activated simultaneously to represent a complex sound with multiple frequency components. For example, such stimulation may result in unpredictable and excessive loudness and loss of spectral shape, that is, the peaks of the frequency-place profile are distorted by the summation of fields.

Almost all successful stimulation strategies in clinical use today circumvent channel interaction by using sequential pulsatile stimulation. Such strategies deliver stimulation through only one channel at any given instant. Stimulation is time-multiplexed across channels at rates high enough to produce a fused percept for the recipient. Although monopoles excite broad spatial extents of the nerve array, spatial/spectral information is nevertheless adequately conveyed, presumably by the trajectory of the centroids of those ranges. In this way a reasonable representation of a sound's time-varying magnitude spectrum can be appreciated by the recipient, such that formant peaks can be perceived.

Prior to the widespread adoption of sequential-monopolar stimulation for clinical use, several more complex channel configurations were explored with the objective of producing more focused electrical fields and hence narrower stimulation regions. These included bipolar stimulation with longitudinally-, radially-, and obliquely-oriented dipoles, tripoles or quadrupoles, common ground, and complex multipolar channels derived by so-called "current deconvolution." These more complex channel configurations have not resulted in speech understanding gains.

SUMMARY

In one aspect of the invention, a cochlear implant is disclosed, the cochlear implant configured to provide stimulation of a discrete stimulation region of a particular recipient's cochlear, said discrete stimulation region being defined by interference of stimulating and limiting signals simultaneously applied to electrode channels of an electrode array implanted in the cochlear, wherein the stimulating and limiting signals are determined based upon transimpedance measurements representing specific spread functions of the particular recipient.

In another aspect of the invention, a method for providing stimulation of a discrete stimulation region of a particular recipient's cochlear is disclosed. The method comprises: measuring recipient-specific current spread functions in the form of a matrix of transimpedance values between stimulated and idle electrodes; computing an inverse matrix of transadmittance values is computed using the measured transimpedance values; and utilizing the matrix of transadmittance values to determine the required vector of electrode currents that will produce the desired vector of stimulating voltages.

BRIEF DESCRIPTION OF THE DRAWINGS

Embodiments of the present invention will be described in conjunction with the accompanying drawings, in which:

FIG. 4 is a flowchart of the operations performed in accordance with one embodiment of the present invention;

DETAILED DESCRIPTION

Embodiments of the present invention are directed to a medical stimulation device such as a cochlear implant that, when operably implanted in a recipient's cochlear, provides stimulation of one or more spatially-restricted contiguous portion(s) of the spiral array of auditory nerve fibers in the cochlear, referred to herein as discrete stimulation regions. Each discrete stimulation region is defined by the constructive and/or destructive interference of stimulating and limiting signals simultaneously applied to electrode channels of an implanted electrode array, the stimulating and limiting signals being determined based upon transimpedance measurements of intracochlear electrode channels of the implanted electrode array representing specific spread functions of an individual recipient.

In certain embodiments the stimulating signal is applied through a targeted electrode channel; that is, one or more successive electrodes which is/are adjacent to the discrete stimulation region. The targeted electrode channel is selected to represent a sound based on the outputs of a sound processor to stimulate neural activity in the discrete stimulation region to thereby cause a percept of the represented sound. The size of the discrete stimulation region is defined by the limiting signal(s) applied to electrode channel(s) other than the targeted electrode channel, and which negate(s) current spread which would otherwise occur in response to the stimulating signal. Thus, electrodes of the electrode array may either apply a stimulating signal, no signal or a limiting signal.

Once having read the present application, one of ordinary skill in the art would appreciate that various combinations of stimulating and limiting signals may be used to negate the effects of current spread and to provide precise stimulation for spatial-temporal applications.

Figure 3:
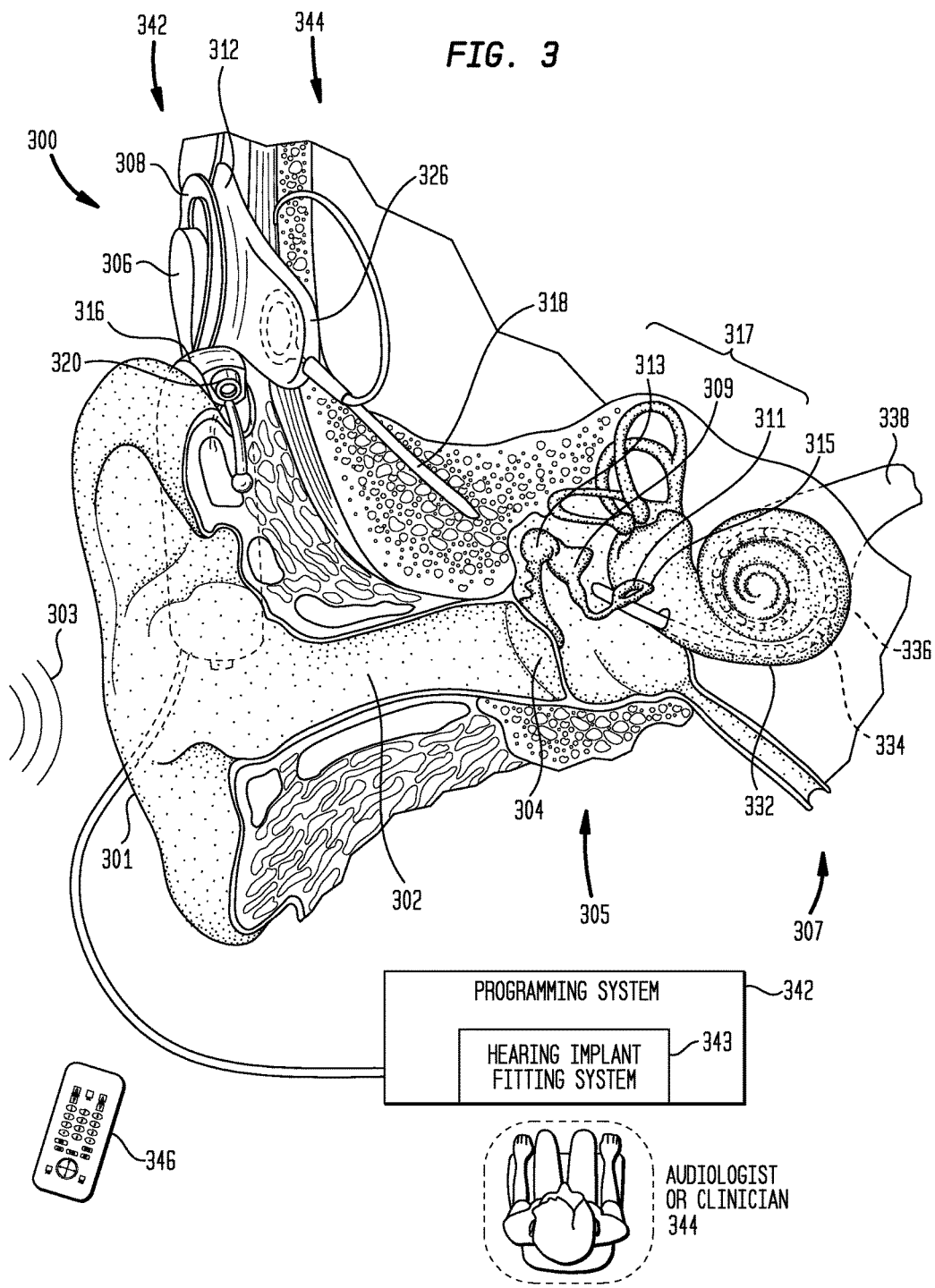
FIG. 3 is a diagram of the components of an exemplary cochlear implant in which embodiments of the present invention may be advantageously implemented.

There are a variety of stimulating medical devices in which embodiments of the present invention may be advantageously implemented. FIG. 3 is a perspective view of an exemplary stimulating prosthetic hearing implant, a cochlear implant 300 in which an embodiment the present invention is implemented. The relevant components of outer ear 301, middle ear 305 and inner ear 307 are described next below, followed by a description of cochlear implant 300.

An acoustic pressure or sound wave 303 is collected by outer ear 301 (that is, the auricle) and channeled into and through ear canal 302. Disposed across the distal end of ear canal 302 is a tympanic membrane 304 which vibrates in response to acoustic wave 303. This vibration is coupled to oval window or fenestra ovalis 315 through three bones of middle ear 305, collectively referred to as the ossicles 317 and comprising the malleus 313, the incus 309 and the stapes 311. Bones 313, 309 and 311 of middle ear 305 serve to filter and amplify acoustic wave 303, causing oval window 315 to articulate, or vibrate. Such vibration sets up waves of fluid motion within cochlea 332. Such fluid motion, in turn, activates tiny hair cells (not shown) that line the inside of cochlea 332. Activation of the hair cells causes appropriate nerve impulses to be transferred through the spiral ganglion cells (not shown) and auditory nerve 338 to the brain (not shown), where they are perceived as sound.

Cochlear prosthesis 300 comprises external component assembly 342 which is directly or indirectly attached to the body of the recipient, and an internal component assembly 344 which is temporarily or permanently implanted in the recipient.

External assembly 342 typically comprises a sound transducer 320 for detecting sound, and for generating an electrical audio signal, typically an analog audio signal. In this illustrative embodiment, sound transducer 320 is a microphone. In alternative embodiments, sound transducer 320 may comprise, for example, more than one microphone, one or more telecoil induction pickup coils or other device now or later developed that may detect sound and generate electrical signals representative of such sound.

External assembly 342 also comprises a speech processing unit 316, a power source (not shown), and an external transmitter unit 306. External transmitter unit 306 comprises an external coil 308 and, preferably, a magnet (not shown) secured directly or indirectly to the external coil 308.

Speech processing unit 316 processes the output of microphone 320 that is positioned, in the depicted embodiment, by outer ear 301 of the recipient. Speech processing unit 316 generates coded signals, referred to herein as a stimulation data signals, which are provided to external transmitter unit 306 via a cable (not shown). Speech processing unit 316 is, in this illustration, constructed and arranged so that it can fit behind outer ear 301. Alternative versions may be worn on the body or it may be possible to provide a fully implantable system which incorporates the speech processor and/or microphone into the internal component assembly 344.

Internal components 344 comprise an internal receiver unit 312, a stimulator unit 326 and an electrode assembly 318. Internal receiver unit 312 comprises an internal transcutaneous transfer coil (not shown), and preferably, a magnet (also not shown) fixed relative to the internal coil. Internal receiver unit 312 and stimulator unit 326 are hermetically sealed within a biocompatible housing. The internal coil receives power and data from external coil 308, as noted above. A cable or lead of electrode assembly 318 extends from stimulator unit 326 to cochlea 332 and terminates in an array 334 of electrodes 336. Signals generated by stimulator unit 326 are applied by electrodes 336 to cochlear 332, thereby stimulating the auditory nerve 338.

In one embodiment, external coil 308 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 312 may be positioned in a recess of the temporal bone adjacent to outer ear 301 of the recipient.

It should be appreciated that, as noted elsewhere herein, embodiments of the present invention may be implemented in stimulating prosthetic hearing implants other than cochlear implant 300. For example, while cochlear implant 300 is described as having external components, in alternative embodiments, cochlear implant 300 may be a totally implantable prosthesis. In one exemplary implementation, for example, sound processing unit 316, including microphone 320, a sound processor and/or a power supply may be implemented as one or more implantable components.

As shown in FIG. 3, cochlear implant 300 is further configured to interoperate with a wireless user interface 346 to facilitate implant configuration and control by the recipient, and an external processor 342 such as a personal computer, workstation or the like, implementing a hearing implant fitting system.

As one of ordinary skill in the art will appreciate, the present invention may be used in connection with any speech strategy now or later developed, including but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. The present invention may also be used with other speech coding strategies now or later developed. Among other things, these strategies offer a trade-off between temporal and spectral resolution of the coded audio signal by changing the number of frequency channels chosen in the signal path.

As noted, channel interaction may limit the effectiveness of a cochlear implant. In particular, because of channel interaction, speech strategies which simultaneously stimulate multiple electrodes have only limited clinical success. Various methods have been devised over the years to address the problem of current spread to minimize the resulting channel interaction.

Figure 1:
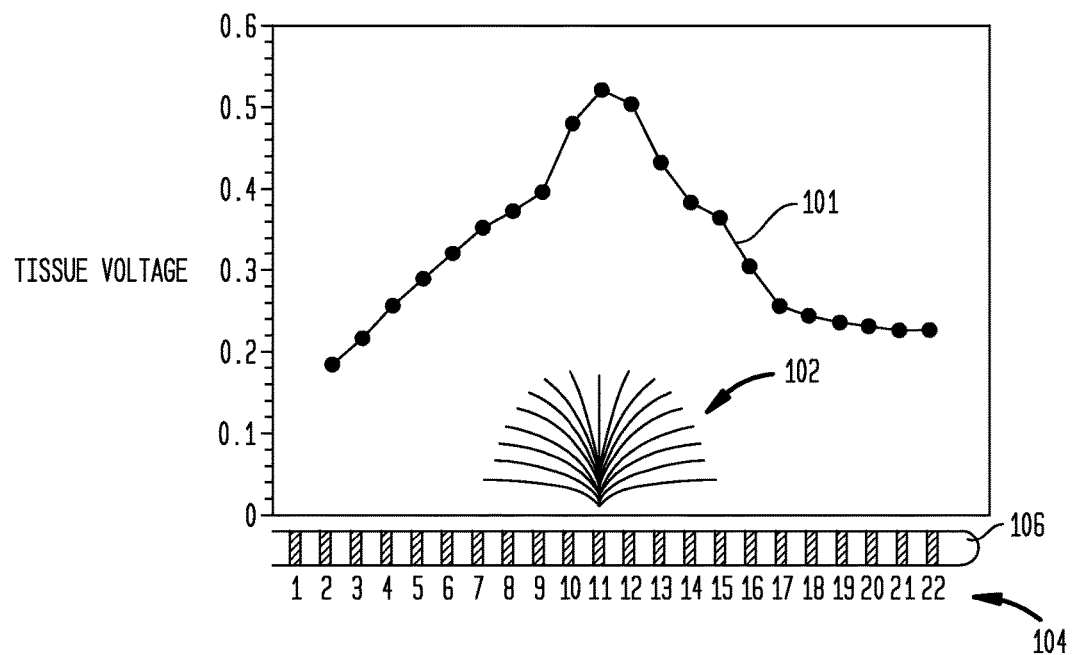
FIG. 1 shows a graph illustrating the voltage generated in various regions in a tissue in response to the application of current to one tissue region.
Figure 2:
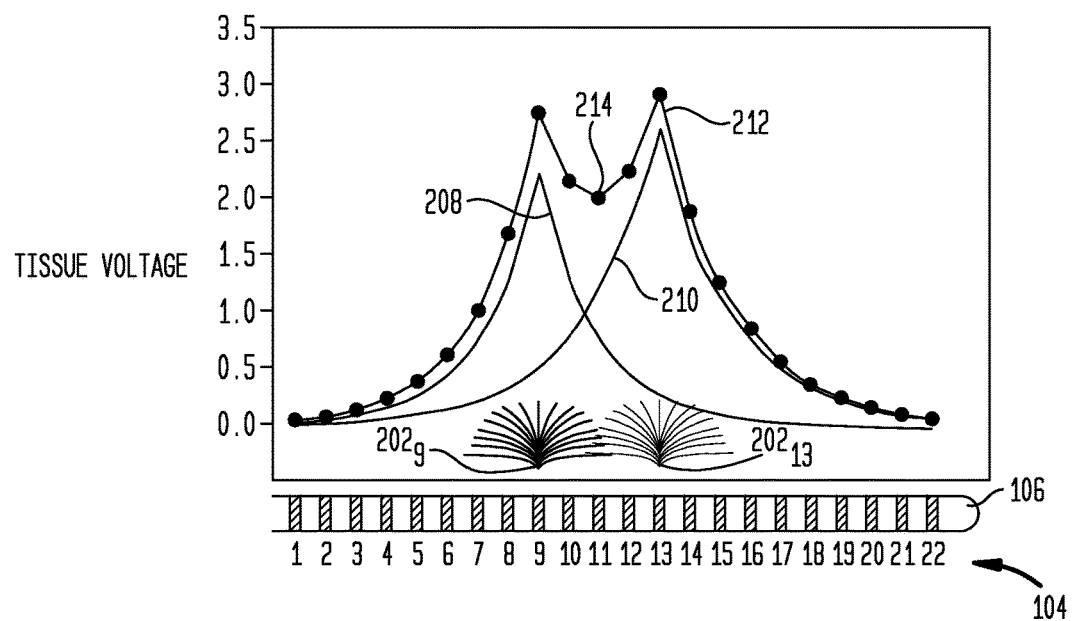
FIG. 2 shows a "current spread" graph when two electrodes are stimulated and the corresponding electrode array.

The most effective approach has been the adoption of so-called "sequential" stimulation strategies, wherein only one electrode produces current at any given moment. Since no two electrodes generate stimulating voltages simultaneously, the summation of FIG. 2 is not likely to occur. By rapidly sequencing the stimulating current among selected electrodes, a percept may be generated that is "apparently" simultaneous.

Sequential stimulation avoids the difficulties of loudness summation, but does not avoid the fundamental problem that a stimulus intended to stimulate only one pitch region, i.e. nerve region, may broadly stimulate many pitch regions. Thus, sequential stimulation may not produce excitation only at the desired region(s). Sequential stimulation also imposes serious timing constraints that prevent conveyance of some temporal structures contained in a sound. If two components of a sound would call for stimulation of two electrodes at the same moment in time, the sequential strategies forbid this. Harmonic relationships and other temporally-encoded cues may be seriously compromised as well. Although, sequential pulsatile strategies have been adopted to circumvent some of the worst effects of channel interaction, those strategies, along with the current spread itself, impose significant constraints on the temporal and spatial patterns of nerve activity that can be artificially produced with a cochlear implant.

Previous stimulating methods to overcome these limitations have not met with success. These methods are described in U.S. Pat. No. 4,648,403; Van Compernolle, Dirk, "Speech Processing Strategies for a Multichannel Cochlear Prosthesis," *Ph.D. Dissertation, Stanford University* (1985); Van Compernolle, Dirk, "A computational model of the cochlea used with cochlear prosthesis patients," in: *Acoustics, Speech, and Signal Processing, IEEE International Conference on ICASSP* '85, Volume 10, pp. 427-429 (1985); White, R L and Van Compernolle, D, "Current spreading and speech-processing strategies for cochlear prostheses," *Ann. Otol. Rhino. Laryng.* 96 (Suppl.

128), 22-24 (1987); Townshend B, et al., "Pitch perception by cochlear implant subjects," *J. Acoust. Soc. Am.,* 82(1): 106-115 (1987); Townshend B, and White R L, "Reduction of Electrical Interaction in Auditory Prostheses," *IEE Tran. Biomd. Eng.* BME-34:891-897 (1987), the entire contents and disclosures of which are hereby incorporated by reference herein. These conventional stimulating methods are limited by psychophysical measures of current spread, which are tedious and time consuming, and may produce computed solutions requiring enormous current. A further significant drawback is that psychophysical measures of current spread provides only an imprecise measure of the physical parameters of interest.

Bipolar stimulation, where current flows from one electrode to another nearby electrode, partially reduces channel interaction, but at the expense of significantly increased current requirements. The resulting improvement in spatial sharpening has generally been modest.

Prior tripolar or quadrupolar electrode configurations have been described as a means for narrowing the stimulus area of an electrode. Certain embodiments of such configurations are described in Jolly C N, Spelman F A, Clopton B M, "Quadrupolar stimulation for Cochlear prostheses: modeling and experimental data," *IEEE Trans. Biomed. Eng.* 43(8):857-865 (1996); Clopton & Spelman, "Electrode configuration and spread of neural excitation: compartmental models of spiral ganglion cells," *Ann. Otol. Rhinol. Laryngol.* 166:115-118 (Suppl. 1995); Miyoshi, et al., "Proposal of a new auditory nerve stimulation method forcochlear prosthesis," *Artif. Organs* 20:941-946 (1996); Kral, et al., "Spatial resolution of cochlear implants: the electrical field and excitation of auditory afferents," *Hear Res.* 121:1128 (1998); Townshend, et al., "Pitch perception by cochlear implant subjects," *J. Acoust. Soc. Am.* 82(1):106-115 (1987), the entire contents and disclosures of which are hereby incorporated by reference herein. The above and other prior art tripolar/quadrupolar approaches utilize fixed weights based upon mathematical models, or physiological measurements, and do not contemplate consideration of the individual recipients. Further, conventional tripolar/quadrupolar approaches generally ignore contributions from other more distant electrodes thereby limiting their ability to sharpen the field.

Embodiments of the present invention each overcome one or more of the above and other constraints and may allow any spatio-temporal pattern of excitation, within the spatial resolution of an electrode array. Embodiments of the present invention stimulate discrete nerve regions through the constructive and destructive interference of stimulating signals and interfering limiting signals, which may be of the same or opposite polarity, applied via multiple electrode channels of the electrode array. This interference generates a stimulating voltage at a discrete stimulation region within the cochlea. The stimulating and limiting signals are determined based upon transimpedance measurements from electrodes within the cochlea.

One advantage of this stimulation method is that the implemented strategy is customized to the recipient to improve his/her hearing response. Also, embodiments of the present invention may provide a substantial improvement in sound representation, better speech understanding, and improved recognition of musical information, such as melody and harmonic relationships.

In one embodiment of the present invention every electrode in the electrode array may apply a stimulating or limiting signal. Some electrodes might be used to select the current balance that minimizes spread of current with a limiting signal. Through the use of voltages at every electrode, the discrete nerve region may be precisely and simultaneously controlled using proper sources and sinks at each electrode. Thus, a recipient may receive a customized solution for determining the necessary current weights to improve hearing.

In certain embodiments, the stimulation involves a contribution from every electrode to every voltage. Further embodiments may apply a similar concept to a subset of electrodes. For certain applications and implants, such further embodiments may be advantageous, because fewer current sources and/or arithmetic operations may be required. For example, tripolar stimulation has previously been suggested as a possible means of ameliorating current spread. In a tripolar configuration, some of the current flowing from a center electrode returns to each of two neighboring electrodes, and some may return to a distant electrode, i.e. an electrode outside of the cochlea. Tripolar configurations described in the literature involve fixed weights, such as 30% of the current to each neighbor, and 40% to the distant electrode. But due to anatomical and positioning variations the optimal weights for minimizing current spread with a tripole would generally be different for each group of three electrodes. In contrast, embodiments of the present invention having phased-array stimulation are not subject to such restrictions, and may be used to customize the individual the weights for each tripolar group of electrodes. Other embodiments combine positive and negative currents of appropriate magnitude through more than one electrode to create a desired profile of stimulating voltages across N electrode sites.

FIG. 4 is a flow chart of the operations performed in accordance with one embodiment of the present invention. The operations are described next below with reference to additional FIGS. 5A and 5B. At block 402, recipient-specific current spread functions are measured in the form of a matrix of transimpedance values between stimulated and idle electrodes.

For each intracochlear electrode, a monopolar biphasic pulse is delivered in one embodiment of the present invention. When a monopolar current is passed through an intracochlear electrode 504 a corresponding voltage can be measured at any other intracochlear electrode 504. The transimpedance between the two electrodes is defined as the ratio of the measured voltage to the delivered current. For frequencies of interest in cochlear applications, the cochlear fluids and tissue are essentially resistive such that the voltage is approximately instantaneously proportional to the current to a close approximation. Thus the reactive component of the transimpedance may be ignored. Nevertheless, the term transimpedance is used throughout this application in preference to transresistance as a reminder that the analysis presented herein may be carried out with complex arithmetic in those applications in which reactive components are nonnegligible.

For each intracochlear electrode 504, a monopolar biphasic pulse is delivered at the maximum comfortable current level. Return current is measured, for example, at one or more extra-cochlear electrodes, the arrangement of which is well-known in the art. The voltage pulse at each of the remaining electrodes 504 is measured. In one embodiment, the phase width is selected to be long enough for the voltage pulse waveform to plateau, but short enough to permit relatively high currents while remaining comfortable, thus maximizing the signal-to-noise ratio of the voltage measurement. Based on the applied current and measured voltage, the transimpedance of each combination of electrodes is determined as described below.

Figures 5A, 5B:
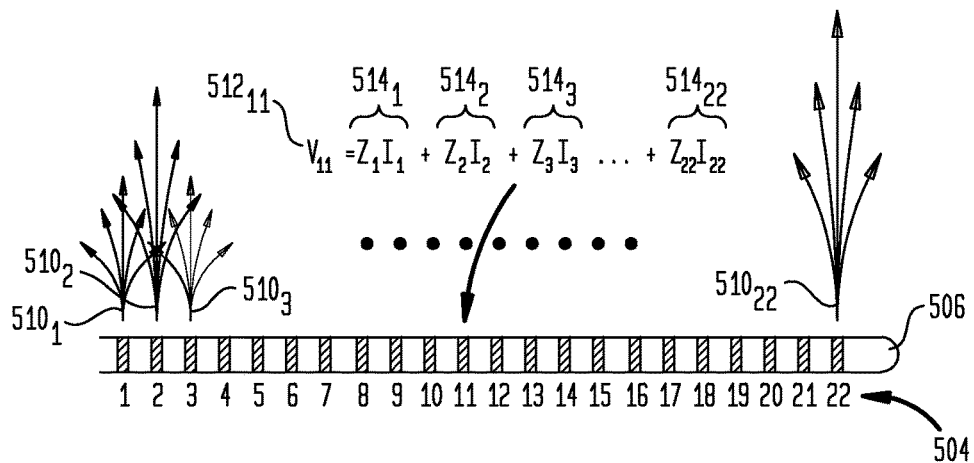
FIG. 5A shows a graph of the components of stimulating signal in accordance with an embodiment of the present invention.
FIG. 5B shows equations used to construct stimulating and limiting signals in accordance with an embodiment of the present invention.

Referring to FIG. 5A, each current $I_1$ through $I_{22}$ flowing simultaneously through each of the 22 different electrodes 504 results in a current spread $510_1$ through $510_{22}$, respectively. The instantaneous voltage 512 $V_1 \ldots V_{22}$ adjacent to each electrode 504 is the sum of 22 separate components $514_1$ through $514_{22}$. Each component 514 is proportional in magnitude and sign to the current from one of the electrodes 504 $I_1 \ldots I_{22}$ (in units of mA), represented by the corresponding measured transimpedance value, $z_1$ $z_{22}$ (in units of V/mA (k$\Omega$)). Thus the stimulating voltage $512_{11}$ at the site of electrode 11 may be expressed as a weighted sum of the weighted currents through all stimulating electrodes, as shown in FIG. 5A and Equation (1) below:

$$V_{11} = Z_1 I_1 + Z_2 I_2 + \ldots + Z_{22} I_{22} \qquad (1)$$

A similar equation may be written for the voltage adjacent to each of the other electrodes 504 as shown in FIG. 5B. Thus, in a 22 electrode system, 22 simultaneous equations may be written which describe the voltage applied to the nerve region adjacent to each electrode as a weighted sum of the same set of 22 currents h . . . 122. The set of 22 simultaneous equations in FIG. 5B, where each weight, transimpedance Z, now has two subscripts, one indicating the associated current, and one indicating the electrode site whose voltage is being summed The set of simultaneous equations in FIG. 5B, may be represented in vector/matrix notation as shown in Equation (2):

$$v = Z i_e \qquad (2)$$

where $I_e$ represents the column vector of 22 currents $I_1 \ldots I_{22}$ flowing through the electrode, Z represents the square matrix of weights $z_{1,1} \ldots z_{22}$, and V represents the column vector of 22 stimulating voltages $V_1 \ldots V_{22}$ at the discrete stimulation regions adjacent the corresponding electrodes $I_1 \ldots I_{22}$.

As noted, both the currents and voltages are represented as functions of time, indicating that the matrix equation represents an instantaneous calculation. It should be appreciated, however, that as noted above, the preferred embodiment uses simple scalar values. This reflects the assumption that voltages are instantaneously proportional to currents (equivalent to assuming that the tissue impedances is purely resistive with no reactive component). So if a current changes, all resulting voltages change instantaneously and proportionally. While this is a relatively accurate approximation, it is not exactly correct. At the expense of greatly increased computational burden, embodiments of the invention may be practiced using complex values in the matrices, recognizing the reactive (non-resistive) part of the relationship between currents and voltages. Then instead of being functions of time, the variables in equations 1 and 2 would be functions of the Laplace transform variable s.

For a stimulating electrode j and measuring electrode i, transimpedance $z_{ij}$ has units of V/mA (k$\Omega$) and is given by Equation (3):

$$z_{ij} = v_i / i_j \qquad (3)$$

where, $v_i$ is the measured peak voltage at measuring electrode i, and $i_j$ is the amplitude of the current pulse applied to electrode j. In this way a 22×22 matrix $Z_m$ of transimpedance values may be determined for each recipient, as shown in Equation (4):

$$Z_m = \begin{bmatrix} z_{1,1} & z_{1,2} & \cdots & z_{1,22} \\ z_{2,1} & z_{2,2} & \cdots & z_{2,22} \\ \vdots & \vdots & \ddots & \vdots \\ z_{22,1} & z_{22,2} & \cdots & z_{22,22} \end{bmatrix} \qquad (4)$$

Each column p of the matrix represents the spread function for stimulation through electrode p, with a peak at the diagonal value $z_{pp}$. The values on the diagonal of $Z_m$, typically can not be measured explicitly due to polarization effects. A current-carrying electrode is polarized by electrochemical gradients that arise across the metal/electrolyte boundary. This precludes using the same electrode both to deliver current and to measure potential in the cochlear fluid. Instead, values on the diagonal may be extrapolated, preferably using the highest slope among adjacent pairs in the same row and column to avoid underestimating the sharpness of the spread function, as this would result in unnecessarily high peak currents in the focused stimuli. The effect of errors among the extrapolated values is considered below.

As one of ordinary skill in the art would appreciate, the matrix $Z_m$ is very nearly diagonally symmetric. For example, for a three-port network where a single node serves as both the return current path and the voltage measurement reference, the reciprocity theorem holds that diagonal symmetry obtains—i.e. $z_{ij} = z_{ji}$ for all i and j.

In fact, due to the noted polarization phenomenon, the extracochlear electrodes could not serve as both return current path and voltage reference. Instead, a surface electrode on the recipient may serve as the reference. However the observed deviations from diagonal symmetry were small and comparable to the noise in the measurements. This implies that the tissue adjacent the return electrode is essentially neutral, or equipotential with the external electrode, and that the voltage gradients of consequence occur within and about the cochlea. Therefore it may be assumed that deviations from diagonal symmetry are dominated by noise in the measurement. In order to reduce this noise the diagonally opposite elements may be averaged to compute a new transimpedance matrix, as shown in Equation (5):

$$z = \frac{1}{2}(Z_m + Z_M^T) \qquad (5)$$

where $Z_M^T$ denotes the transpose of $Z_m$ (matrix Z is diagonally symmetric by definition).

Certain embodiments take advantage of the Reciprocity Theorem to avoid measuring the entire forward matrix [z], omitting measurement of cells above the main diagonal of matrix [z]. The unmeasured values are then filled in by transposing values from below the main diagonal. Alternatively, embodiments may omit the measurement of cells below the main diagonal, and fill these measurements by transposing values from above. In either case such embodiments may reduce the number of measurements needed to determine matrix [z] by half.

Figure 6A:
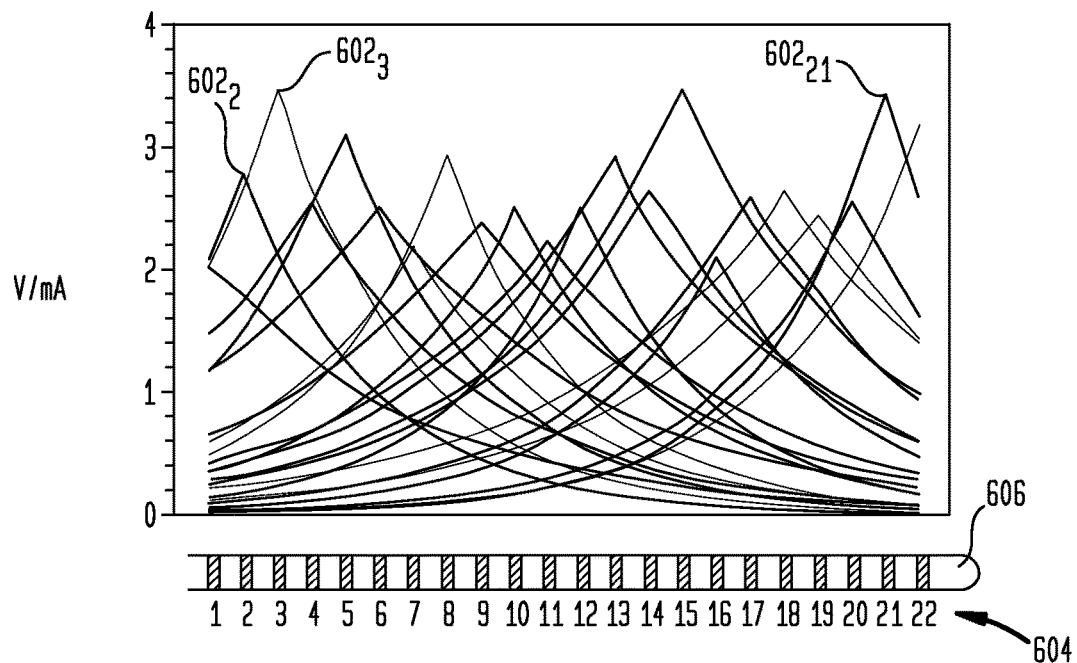
FIG. 6A is a graph showing voltage profiles generating by applying the same current to each electrode of an electrode array.

FIG. 6A is a graph showing a set of voltage profile curves $602_1 \ldots 602_{22}$ arising from stimulation of one electrode 604 at a time from an electrode array 606. The vertical values, in V/mA, of the points on each curve 602 represent one column of the transimpedance matrix [z] shown in FIG. 5B. Curve $602_1$ represents the first column of FIG. 5B, curve $602_2$ the second column, curve $602_3$ the third column, and so on. Each voltage profile curve 602 is produced by passing 1 mA through each electrode 604. Curves 602 may have differing peak values and widths depending on a variety of factors including the type of electrode array used, how the electrode array is implanted and the recipient.

The forward matrix [z] may also be determined as follows. A fixed amplitude current waveform is applied to a single electrode (number j) with respect to a distant electrode. The corresponding voltage waveform may be measured at each of the other unstimulated electrodes with respect to a non-current carrying reference electrode at a neutral site in the tissue. Signal averaging may be used as necessary to obtain a clean measurement. Some feature of the stimulus waveform is selected for computing the ratio of voltage to current. For example, if the stimulus current is a rectangular biphasic pulse, the peak of the first phase could serve as a reference feature. The value for $z_{ij}$ would be equal to the ratio of the peak voltage on electrode i to the peak current flow through electrode j. This set of measures would be used to define one column of [z] except for the entry $z_{jj}$, the weight for the stimulated electrode, for the reasons noted above. The missing value of $z_{jj}$ may be estimated by extrapolating from curve(s) fitted through several values above and/or below electrode j. The entire process above may be repeated for each stimulating electrode to populate the entire forward matrix [z].

The required voltage measurements may be carried out in any location internal or external to cochlear implant 100, such as in sound processor 316, computer 342, etc., and the transimpedance values or representations thereof may be transmitted via to sound processor 316 and stimulator unit 326 as necessary.

Returning to FIG. 4, at block 404, an inverse matrix of transadmittance values is computed using the computed transimpedance values. The matrix of transadmittance values is utilized to determine the required vector of electrode currents that will produce the desired vector of stimulating voltages. As will be described below, each column of the transadmittance matrix comprises a set of numerical weights (transadmittance values) defining the current contribution from each electrode that is required to produce a non-zero intrascalar voltage at a single discrete stimulation region. As such, each such vector of weights defines an electrode channel.

Because Z is square, and provided that it is nonsingular, we can compute its inverse $Y=Z^{-1}$. Then solving equation (3) for $i_e$ yields equation (6):

$$i_e = Z^{-1} v_d = Y v_d \quad (6)$$

The elements of Y are transadmittance values with units of mA/V (millimhos).

Equation 6 provides a solution to the inverse problem and from this equation, for any instantaneous set of desired stimulating voltages [V] the instantaneous currents [I] necessary to generate the stimulating voltages may be computed. Embodiments of the present invention may compute that the inverse matrix [z] once, after which it may be used continuously to compute any desired series of currents [I].

The constraint that Z be non-singular is not mathematically problematic, as a singular matrix will not arise with actual weighting constants for an actual electrode set. In practical terms, the corresponding problem is that, if the profiles defined by the rows of Z are quite broad and almost horizontal, its Condition Number may be large, such that the required currents may also be very large.

Figure 6B:
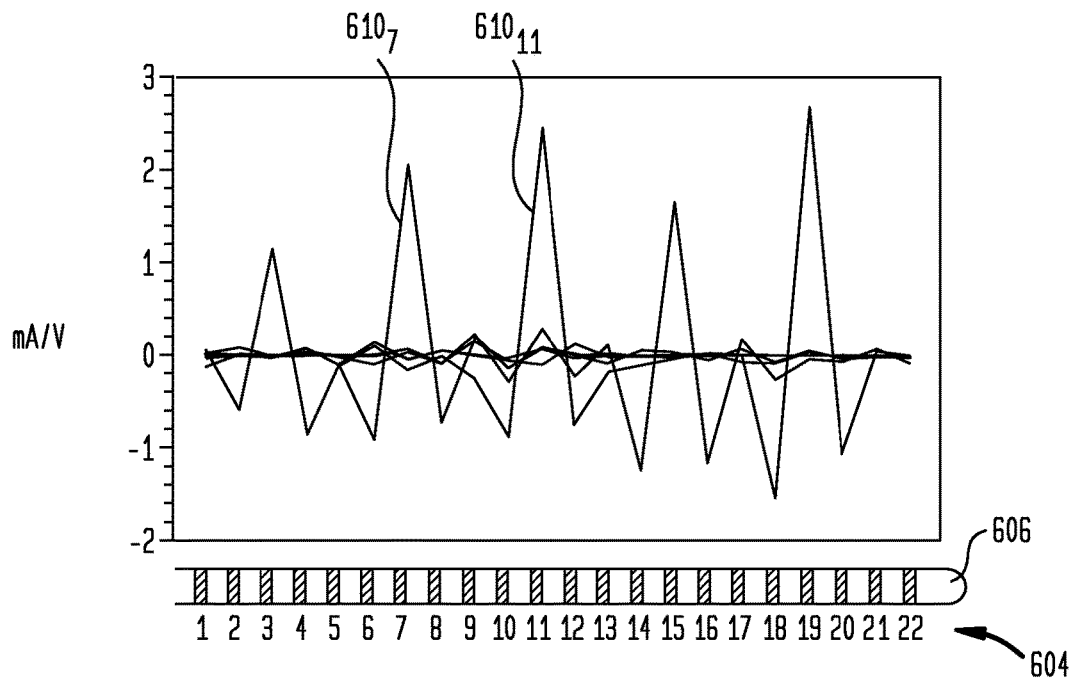
FIG. 6B is a graph showing current levels required to apply a stimulating signal on one electrode while applying a limiting signal on the remaining electrodes in the electrode array.

The graph shown in FIG. 6B shows part of the inverse matrix Y from Equation 6. Each curve 610 represents one column of matrix Y. The vertical values have units of mA/V. FIG. 6B shows the current required from each electrode 604 on an electrode array 606 to generate a stimulating voltage of 1.0 V at a single electrode site, and 0 V at all other electrode sites. For clarity, FIG. 6B shows five of the possible 22 curves. For example, curve 610$_7$ illustrates the currents required on each electrode to generate a stimulating voltage of 1.0 V adjacent to electrode 7 (and 0 V at all other sites). Similarly, curve 61$_{11}$ shows the currents required to generate a 1.0 V stimulating voltage only adjacent to electrode 11.

Producing a specified voltage $v_{d_p}$ at a single discrete stimulation region, p, and exactly zero volts at every other region along the cochlear represents optimally focused single-place stimulation. The required vector of currents is the product of scalar $v_{d_p}$ and column p of Y:

$$i_e = v_{d_p} \begin{bmatrix} y_{1_p} \\ \vdots \\ y_{22_p} \end{bmatrix} \quad (7)$$

The transadmittance elements ($y_{1_p} \ldots y_{22_p}$) of column p constitute a set of 22 signed weights that define the current ratios needed to produce a stimulating voltage only at place p. Thus each column of Y defines a multipolar electrode channel; that is, a set of electrodes among which currents are passed with specified ratios, in order to excite nerve fibers at a single spatially-restricted discrete stimulation region within the cochlea.

Embodiments of the present invention may generate a set of voltages across a 22 electrode array by computing the currents necessary to generate each voltage individually, and then summing the required currents on each electrode. This is equivalent to computing the current vector [I] in Equation 6.

Figure 7:
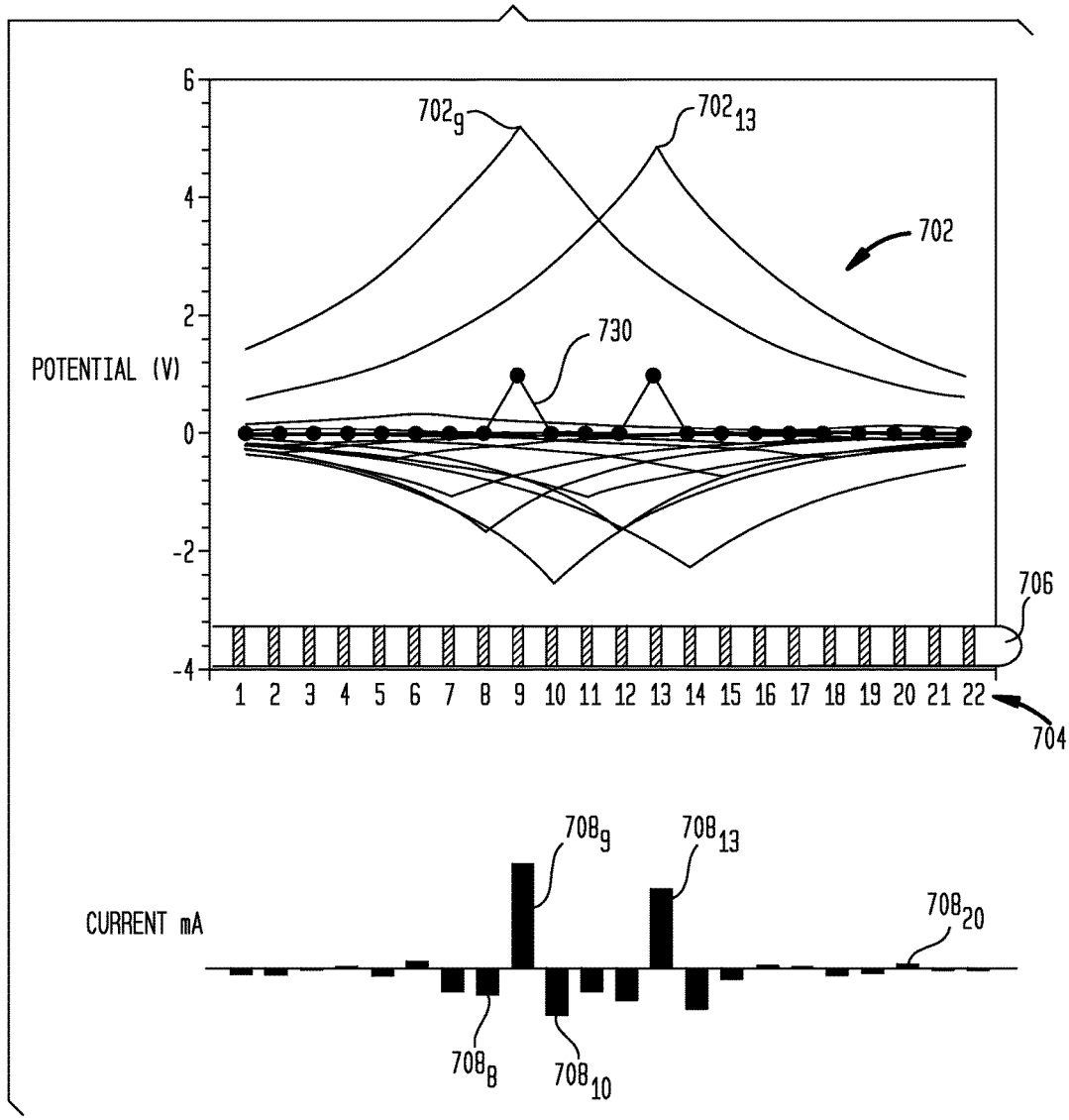
FIG. 7 is a graph showing the voltage profiles and current levels of a phased-array stimulation in accordance with an embodiment of the present invention.

FIG. 7 shows two graphs that illustrate the voltage profile curves 702 and current levels 708 for each electrode 704 on an electrode array 706 to produce 1.0 volt at electrodes 9 and 13, and zero volts on the remaining electrodes 704. On electrode 9 there is a positive current level 708$_9$ corresponding to a stimulating signal. While on the adjacent electrodes 8 and 10 there is a negative current 708$_8$ and 708$_{10}$ corresponding to a limiting signal. On electrode 20 there is a slight positive current 708$_{20}$ which has a limiting signal providing interference.

Net voltage curve 730 is the sum of all of voltage profile curves 702. Net voltage curve 730 represents the stimulating voltage profiles 702 that would arise from the combination of current levels 708. Various combinations of current levels may be generated by embodiments of the present invention to produce desired net voltage to stimulate discrete nerve regions without creating channel interference. Simultaneous stimulation may be achieved by such embodiments.

FIG. 7 also shows the advantages the present invention in preventing channel interference when compared with FIG. 2. In both cases the strategy sought to stimulate only two regions. In the simple case of FIG. 2 the voltage profile was quite different from the intended stimulation. Due to current spread, stimulating voltages were created across the entire length of the electrode array. However by applying the phased-array currents of the present invention, shown in FIG. 7, the profile of stimulating voltages may be precisely achieved.

As is illustrated in FIG. 7, the peak currents required in a phased-array stimulus may be substantially higher than those used for monopolar stimulation. In practice, the broader the single-electrode profiles, shown in FIG. 6A, the higher will be the required currents. As the single-electrode profiles broaden, the Condition Number of the matrix [z]

increases, resulting in higher peak current requirements. Higher currents also imply greater power dissipation within the implanted package. Also, if the curves are very flat and the Condition Number of matrix [z] is large, the method demands greater precision in the arithmetic and current sources, and becomes sensitive to small drifts in the coefficients of [z] and [Y]. For all of these reasons, embodiments of the present invention using phased-array stimulation may be implemented in Nucleus Contour™ or similar implant devices having reasonably sharp single-electrode profiles. Also, when electrodes are positioned along the lateral wall of the cochlea larger current, power and precision requirements may be required.

The values of coefficients in the forward matrix [z] may vary slowly over time due to scar tissue formation around the electrode, bone growth, electrolyte shifts, etc. In that case it may be necessary to remeasure and update the matrices from time to time, such as when visiting a clinic or doctor. It might be possible, for example, for the implant system to remeasure [z] each time the system is turned on.

With existing implant designs, if a current source saturates and is unable to deliver the intended current, the result is benign in that it produces a sound that is less loud than intended. In embodiments of the present invention, the phased-array stimulation may produce loud and possibly uncomfortable sounds when the current source saturates. This may occur when the saturated source fails to cancel in part the current from another unsaturated source. Such embodiments may take precautions by designing an implant that prevents this from occurring, or scales all current sources down when any electrode approaches saturation.

Implementation of a phased-array stimulus of embodiments of the present invention may depend on the presumption that the fluid in the cochlea and tissue are electrically linear and approximately resistive within the frequency range of interest, i.e. up to the highest meaningful spectral component of the stimulus current waveforms. Current preliminary animal and human data support this presumption. As one of ordinary skill in the art would appreciate, alternative embodiments of the present invention may be modified to compensate for non-linear responses of the tissue to changes in the fluid in the cochlea.

In the above embodiments, the stimulation involved a contribution from every electrode to every voltage. A phased-array stimulation of the present invention may also be applied to any subset of M electrodes out of the total N electrodes in an array. For example, with a 22-electrode array, 16 different 7-electrode groups could be formed at one-electrode intervals along the array. The electrodes in any subset need not be contiguous or uniformly spaced. Various combinations of subsets of electrodes are envisaged by the present invention.

Implementations of the present invention may use an imperfect or suboptimal solution when generating the stimulating and limiting signal. An "imperfect solution" or "suboptimal solution," may refer to phase array stimulation that sets the current within a fixed level or constraints. Such a solution may be completely satisfactory for certain recipients and applications, and may provide some practical economy in the implementation. There are two situations where an imperfect solution may be desired. First, if some elements of the matrix [z] are sufficiently small or negligible, these elements may be arbitrarily set to zero without substantially influencing the resulting voltage profile. Such embodiments may reduce computational burden or the number of current sources required. Second, there may be instances where a perfect solution is impractical because such a solution requires peak currents in excess of the implant's capabilities or safety boundaries. In these cases, a suboptimal solution may be created within some set of constraints. For example, the largest current may be less than or equal to 2 mA, and the maximum number of non-zero weights in a column may be less than 10. The suboptimal solution matrix [z] could be designed by optimizing some metric of merit, e.g. mean square deviation from target voltage profile, while meeting the specified constraint.

The present invention may be implemented in implant devices where there are more channels than electrodes. The discussion above describes methods for computing a perfect solution or imperfect solution for N stimulation voltages using N electrodes. Embodiments of the present invention may also generate from the original forward measures [z] an N×L pseudoinverse matrix which would map N currents to L stimulation sites, where L is greater than N. This pseudoinverse may be generated by a least squares fit or other interpolation process beginning with the original transimpedance measures of [z]. A pseudoinverse is described by Van Compernolle, Dirk, "A Computational Model of the Cochlea used With Cochlear Prosthesis Patients," in: *Acoustics, Speech, and Signal Processing, IEEE International Conference on ICASSP '85*, Volume 10, pp. 427-429 (1985), the entire contents and disclosures of which are hereby incorporated by reference herein. In addition, Rodenhiser and Spelman, "A Method for Determining the Driving Currents for Focused Stimulation in the Cochlea," *IEEE Trans. Biomed. Eng.* 42(4) (April 1995) pg. 337-342, which are hereby incorporated by reference herein, described a method for creating a pseudoinverse matrix similar to that of Van Compernolle. However Rodenhiser and Spelman did not teach the use of voltage measurements from unstimulated electrodes to determine the matrix. Instead, Rodenhiser and Spelman proposed use of a mathematical model of fields within a generic cochlea. Such a model approach would not be useful in practice due to individual differences among electrode positions and anatomy of the cochlea across implant recipients.

Matrix Y defines channel weights for the 22 intracochlear electrodes, but each channel also employs extracochlear current as well. The total current flowing into the tissue must equal the total current flowing out. Therefore the extracochlear current must be equal and opposite to the algebraic sum of the intracochlear currents. Its weight $y_{x_p}$ for channel p is given by Equation (8):

$$y_{x_p} = -\sum_i y_{ip} \qquad (8)$$

When comparing stimulation at two places k and p, the fact that $|v_k|>|v_p|$ does not imply that the stimulus at k is functionally stronger than that at p because the magnitude of the biological response depends upon other factors as well (e.g. proximity of contact to the neurons, local neural density). In practice, stimulus intensity for each place is specified independently with respect to some place-specific behavioral criterion level such as detection threshold. We therefore normalized the weights for each channel to produce a dimensionless set of weights $w_p=(w_{1p} \ldots w_{22p})$ as follows:

$$\begin{bmatrix} w_{1p} \\ \vdots \\ w_{22p} \end{bmatrix} = \frac{1}{y_{pp}} \begin{bmatrix} y_{1p} \\ \vdots \\ y_{22p} \end{bmatrix} \quad (9)$$

The extracochlear current weight is similarly normalized as $w_{x_p} = y_{x_p}/y_{pp}$.

As expected, for each channel p diagonal element $y_{pp}$ was invariably the largest of the original channel weights. Thus the largest normalized weight $w_{pp}$ was equal to 1.0. Normalization of the weights preserves the ratios of currents used for stimulation through a single channel p, so that it still produces exactly 0V at all other places k≠p.

The normalized channel weights form the columns of a new matrix W that was used to compute current vectors for experimental stimulation. The input was no longer a vector of desired voltages. Instead the currents were computed from Equation (10):

$$i_e = w i_c \quad (10)$$

where input $i_c$ was a vector of stimulus intensities expressed as "on-center" currents (in mA). The on-center current for a channel is its contribution to the current carried by the electrode located at its stimulation place, while it contributes smaller currents of equal or opposite polarity to the other "off-center" electrodes. Specifying a channel's stimulus intensity in mA this way has the advantage that it allows intuitive comparison with monopolar channels that deliver on-center current only.

Equation (9) provides an instantaneous solution to the inverse problem. In practice each of the stimulus intensities $(i_{c_1}(t) \ldots i_{c_{22}}(t))$ is a function of time. For example those functions might be a set of biphasic pulse trains with varying intensities and pulse widths, or sinusoids of varying frequency and amplitude. Consequently the electrode currents $i_{e_1}(t) \ldots i_{e_{22}}(t))$ are also functions of time. A new current vector $i_e$ must be computed each time that any signal $i_{c_p}(t)$ changes value. In general for sampled signals, a new matrix multiplication is required for every sample interval. Thus by applying electrode current waveforms $i_e(t)$ derived from repeated solution of equation (10) it is possible to deliver 22 completely independent stimulus waveforms to each of the 22 intracochlear places.

As noted the diagonal elements of matrix Z were necessarily estimated by extrapolation from surrounding values. It is important to understand the extent to which estimation errors compromise the resulting stimulation voltages.

If Z is the true transimpedance matrix, we define the imperfect matrix Z' as $$z' = z + \Delta \quad (11)$$

where $\Delta$ is the diagonal matrix of estimation errors $\delta_{pp} = z'_{pp} - z_{pp}$. Using imperfect transimpedances Z' and given a desired vector of stimulating voltages vd the solution of equation (5) yields an imperfect vector $i'_e$ of stimulating currents $$i'_e = z'^{-1} v_d \quad (12)$$

The question at hand is this: "When the imperfect currents of vector $i'_e$ are passed through the electrodes how will the actual voltages v' differ from the desired voltages $v_d$?" From equation (2) the actual voltages are given by $$v' = Z i'_e \quad (13)$$

This may be compared with the correct voltages $v_d$ that would have arisen if the transimpedances really were given by Z'. From equation (12), then:

$$v_d = Z' i'_e \quad (14)$$

Subtracting equation (14) from equation (13) yields the vector of error voltages $\varepsilon$:

$$\begin{aligned} \varepsilon &= v' - v_d \\ &= Z i'_e - Z' i'_e \\ &= (Z - Z') i'_e \\ &= -1 \Delta i'_e \end{aligned} \quad (15)$$

Two observations from equation (15) are noteworthy. First, since $\Delta$ is diagonal, the error voltage $\varepsilon_p$ at place p is determined entirely by the corresponding estimation error $\delta_{pp}$ and the current through electrode p:

$$\varepsilon_p = -\delta_{pp} i'_{ep} \quad (15)$$

Second, the negative multiplier of equation (16) indicates that overestimating the transimpedance $z_{pp}$ results in a weaker than intended voltage and vice versa.

There are many advantages due to embodiments of the present invention. For example, a renewed interest in stimulus focusing has developed in recent years, motivated in part by the demands of strategies that seek to preserve within-channel fine temporal patterns of stimulation. These strategies deliver stimuli at instants in time determined from features of a processing channel's audio filter output (e.g., peaks or zero crossings). In general, those instants in time are asynchronous across channels, and so cannot satisfy the nonsimultaneity constraint of sequential stimulation. As a result, stimulus pulses inevitably will overlap in time resulting in overlapping stimulus regions which corrupt the temporal patterns. That is, due to the overlapping stimulus regions, any given neuron will generally be driven by pulses from multiple channels, receiving the composite of multiple temporal patterns rather than one. The narrowing of the stimulation regions minimizes or prevents this from occurring.

Another advantage of the present invention is the improved representation of periodicity (musical) pitch by an implementing cochlear implants. Besides its importance for music, pitch recognition is important for segregating one voice from multiple competitors and for transmission of semantic information in tonal languages. Perhaps ironically, periodicity pitch is only weakly conveyed by the repetition rate of an electrical stimulus, and then only for an isolated single frequency (as opposed to a chord) and over a limited frequency range. There is growing evidence that recognition of periodicity pitch by the central nervous system may depend upon detecting fine spatial patterning of harmonic complexes. The significantly improved focusing of the stimulation enables an implementing cochlear implant to recreate these detailed spatial patterns.

Although the present invention has been fully described in conjunction with several embodiments thereof with reference to the accompanying drawings, it is to be understood that various changes and modifications may be apparent to those skilled in the art. For example, in one embodiment, the limiting signals have a current which has a polarity opposite to that of the stimulating signal. In other embodiments, the limiting signal may also have a current of equal polarity such that a desired total net stimulation occurs at the discrete region. As another example, the embodiments of the present invention the electrodes are evenly spaced. In alternative embodiments, however, the electrodes have non-uniform spacing. Such changes and modifications are to be understood as included within the scope of the present invention as defined by the appended claims, unless they depart therefrom.

All documents, patents, journal articles and other materials cited in the present application are hereby incorporated by reference herein.

What is claimed is:

1. A method for stimulating at least one discrete stimulation region in a recipient of an implantable hearing prosthesis comprising an electrode array implanted in the recipient, the method comprising:
    delivering one or more stimulating signals via at least one of a plurality of electrode channels of the electrode array implanted in the recipient;
    delivering one or more limiting signals via one or more electrode channels of the plurality of electrode channels of the electrode array such that the one or more stimulating signals and the one or more limiting signals are delivered during overlapping time periods and interfere with one another, wherein the one or more limiting signals have an opposite polarity as the one or more stimulating signals, and wherein the interference defines the at least one discrete stimulation region; and
    wherein the one or more stimulating signals and the one or more limiting signals are based upon transimpedance measurements among the plurality of electrode channels of the electrode array as implanted in the recipient, and wherein the transimpedance measurements represent specific current spread functions of the recipient.

2. The method of claim 1, wherein a size of the at least one discrete stimulation region is defined at least in part by the one or more limiting signals delivered via one or more of the electrode channels other than the at least one electrode channel.

3. The method of claim 1, wherein delivering one or more stimulating signals via the at least one electrode channel, comprises:
    delivering the one or more stimulating signals via successive electrodes of the electrode array.

4. The method of claim 1, wherein delivering one or more stimulating signals via the at least one electrode channel, comprises:
    delivering the one or more stimulating signals via electrodes of the electrode array that are at least one of non-contiguous or non-uniformly spaced.

5. The method of claim 1, further comprising:
    simultaneously delivering at least one additional limiting signal that has a same polarity as the one or more stimulating signals.

6. The method of claim 1, wherein the implantable hearing prosthesis comprises a sound processor configured to process sound signals, and wherein delivering one or more stimulating signals via at least one electrode channel of an electrode array implanted in a cochlea of the recipient comprises:
    delivering stimulating signals generated based operations of the sound processor to evoke perception of a sound in the discrete stimulation region.

7. An implantable hearing prosthesis, comprising:
    an electrode array implantable in a recipient and comprising a plurality of electrode channels; and
    one or more processors configured to:
        generate one or more stimulating signals for delivery to the recipient via at least one of the plurality of electrode channels of the electrode array;
        generate one or more limiting signals for delivery to the recipient via one or more electrode channels of the electrode array, wherein the one or more limiting signals have an opposite polarity as the one or more stimulating signal, and
        wherein the one or more stimulating signals and the one or more limiting signals are delivered during overlapping time periods to the recipient via the electrode array such that the one or more stimulating signals and the one or more limiting signals interfere with one another to define at least one discrete stimulation region in the recipient, and
    wherein the one or more stimulating signals and the one or more limiting signals are based upon transimpedance measurements among the plurality of electrode channels of the electrode array as implanted in the recipient, and wherein the transimpedance measurements represent specific current spread functions of the recipient.

8. The implantable hearing prosthesis of claim 7, wherein the one or more processors are configured to:
    simultaneously generate at least one additional limiting signal that has a same polarity as the one or more stimulating signals.

9. The implantable hearing prosthesis of claim 7, wherein a size of the at least one discrete stimulation region is defined at least in part by the one or more limiting signals delivered via one or more of the electrode channels other than the at least one electrode channel.

10. The implantable hearing prosthesis of claim 7, wherein the one or more stimulating signals are delivered via successive electrodes of the electrode array.

11. The implantable hearing prosthesis of claim 7, wherein the one or more stimulating signals are delivered via electrodes of the electrode array that are at least one of non-contiguous or non-uniformly spaced.

12. The implantable hearing prosthesis of claim 7, wherein the one or more processors are configured to implement a speech strategy comprising one or more of Continuous Interleaved Sampling (CIS), Spectral PEAK Extraction (SPEAK), and Advanced Combination Encoders.

13. The implantable hearing prosthesis of claim 7, wherein the implantable hearing prosthesis is a cochlear implant.

14. A system, comprising:
    an implantable hearing prosthesis implanted in a recipient; and
    a hearing implant fitting system configured to communicate with the implantable hearing prosthesis, and comprising:
    one or more processors configured to:
        obtain, from the implantable hearing prosthesis, measured recipient-specific current spread functions in the form of a matrix of transimpedance values of electrode channels of an electrode array implanted in the recipient's cochlea and having electrodes mounted thereon;
        calculate values for a diagonal of the matrix of transimpedance values using the measured recipient-specific current spread functions;
        compute a matrix of transadmittance values using the matrix of measured transimpedance values; and
        determine, using the matrix of transadmittance values, a vector of electrode currents that will produce a desired vector of stimulating voltages resulting in stimulation of one or more discrete stimulation regions within the recipient; and send the determined vector of electrode currents or representations thereof to the implantable hearing prosthesis.

15. The system of claim 14, wherein to compute the matrix of transadmittance values, the one or more processors are configured to:

compute an inverse of the matrix of measured transimpedance values.

16. The system of claim 14, wherein the implantable hearing prosthesis is configured to:

simultaneously deliver a current through a desired number of the implanted electrodes;

measure an instantaneous voltage at each electrode channel resulting from the current delivery, wherein the voltage at each electrode channel is a weighted sum of the currents through the desired number of electrode channels, and wherein each current is multiplied by a weight factor equivalent to a transimpedance between the electrode channel being measured and the particular electrode channel receiving the current being weighted;

create simultaneous voltage equations for each of the measured voltages;

extract the weight factors from the simultaneous voltage equations; and insert the extracted weight factors into a matrix, wherein each row of the matrix is an ordered collection of the weight factors for a particular voltage equation, and each column of the matrix represents the current spread function for stimulation through a particular electrode channel.

17. The system of claim 16, wherein to create the simultaneous voltage equations the implantable hearing prosthesis is configured to:

use simplified computations that assume that a cochlea tissue of the recipient is purely resistive, thereby resulting in use of non-perfect weight factors in the matrix of transimpedance.

18. The system of claim 16, wherein to create the simultaneous voltage equations the implantable hearing prosthesis is configured to:

use complex values recognizing reactive components of the cochlea tissue of the recipient, thereby resulting in approximately perfect weight factors in the matrix of transimpedance.

19. The system of claim 14, wherein the implantable hearing prosthesis is configured to:

apply a fixed amplitude current waveform through a single electrode channel with respect to an extracochlear electrode of the electrode array;

measure a resulting voltage at each of a desired number of other electrode channels with respect to a non-current carrying reference electrode of the electrode array;

calculate a ratio of each the measured voltage to the current applied through the single electrode channel; and populate a column of a matrix with the calculated ratios.

20. The system of claim 19, wherein to calculate the ratio of each the measured voltage to the applied current, the implantable hearing prosthesis is configured to:

use simplified computations that assume that a cochlea tissue of the recipient is purely resistive, thereby resulting in use of non-perfect values in the matrix of transimpedance.

21. The system of claim 19, wherein to calculate the ratio of each the measured voltage to the applied current, the implantable hearing prosthesis is configured to:

use complex values recognizing reactive components of the cochlea tissue of the recipient, thereby resulting in approximately perfect values in the matrix of transimpedance.

* * * * *